(12) United States Patent
Wen et al.

(10) Patent No.: US 11,172,875 B2
(45) Date of Patent: Nov. 16, 2021

(54) SYSTEMS AND METHODS FOR DYNAMIC RESPIRATION SENSING

(71) Applicant: Cardiac Pacemakers, Inc., St. Paul, MN (US)

(72) Inventors: Gezheng Wen, Shoreview, MN (US); Pramodsingh Hirasingh Thakur, Woodbury, MN (US); John D. Hatlestad, Maplewood, MN (US); Jonathan Bennett Shute, Minnetonka, MN (US); Qi An, Blaine, MN (US); Bin Mi, Arden Hills, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 319 days.

(21) Appl. No.: 16/247,308

(22) Filed: Jan. 14, 2019

(65) Prior Publication Data

US 2019/0223782 A1 Jul. 25, 2019

Related U.S. Application Data

(60) Provisional application No. 62/621,935, filed on Jan. 25, 2018.

(51) Int. Cl.
*A61B 5/08* (2006.01)
*A61B 5/0205* (2006.01)
(Continued)

(52) U.S. Cl.
CPC .......... *A61B 5/4818* (2013.01); *A61B 5/0031* (2013.01); *A61B 5/0205* (2013.01);
(Continued)

(58) Field of Classification Search
CPC .......... A61B 5/08–0826; A61B 5/0205; A61B 5/4809; A61B 5/1116–1118
See application file for complete search history.

(56) References Cited

U.S. PATENT DOCUMENTS 5,974,340 A 10/1999 Kadhiresan
7,186,220 B2 3/2007 Stahmann et al.
(Continued)

FOREIGN PATENT DOCUMENTS

WO WO-2004062484 A2 7/2004

OTHER PUBLICATIONS

Moini, Jahangir, "Cardiopulmonary pharmacology for Respiratory Care", Jones & Bartlett Learning, 2012, Chapter 2, 13 pages.

*Primary Examiner* — Thaddeus B Cox
(74) *Attorney, Agent, or Firm* — Schwegman Lundberg & Woessner, P.A.

(57) ABSTRACT

Systems and methods for sensing respiration from a subject are discussed. An embodiment of a respiration monitoring system may include a respiration analyzer circuit to select a physiologic signal from a plurality of signals of different types indicative of respiration, such as between first and second physiologic signals that are respectively detected using first and second detection algorithms, and to compute one or more respiration parameters using the selected signal. The system may select or adjust a respiration detection algorithm for detecting the respiration parameters. The physiologic signal, or the respiration detection algorithm, may each be selected based on a signal characteristic or a patient condition. A cardiopulmonary event may be detected using the computed respiration parameter.

20 Claims, 7 Drawing Sheets

(51) Int. Cl.
*A61B 5/11* (2006.01)
*A61B 5/00* (2006.01)
*A61B 5/352* (2021.01)
*A61N 1/37* (2006.01)
*A61N 1/362* (2006.01)
*A61N 1/365* (2006.01)
*A61B 5/363* (2021.01)

(52) U.S. Cl.
CPC ............ *A61B 5/0816* (2013.01); *A61B 5/352* (2021.01); *A61B 5/4809* (2013.01); *A61B 5/7282* (2013.01); *A61B 5/0809* (2013.01); *A61B 5/1116* (2013.01); *A61B 5/1118* (2013.01); *A61B 5/363* (2021.01); *A61B 5/6823* (2013.01); *A61N 1/3627* (2013.01); *A61N 1/36514* (2013.01); *A61N 1/3706* (2013.01)

(56) References Cited

U.S. PATENT DOCUMENTS

| | | | |
|---|---|---|---|
| 7,819,804 | B2 | 10/2010 | Hatlestsad et al. |
| 8,551,010 | B2 | 10/2013 | Pu et al. |
| 2012/0004699 | A1* | 1/2012 | Bobgan ................ A61N 1/3706 607/27 |
| 2012/0283527 | A1* | 11/2012 | Pu ........................ A61N 1/3627 600/301 |
| 2013/0053675 | A1* | 2/2013 | Kim ........................ A61B 5/24 600/393 |
| 2014/0309943 | A1* | 10/2014 | Grundlehner ........ A61B 5/7264 702/19 |
| 2016/0029898 | A1* | 2/2016 | LeBoeuf ................ A61B 5/01 600/301 |
| 2017/0128020 | A1* | 5/2017 | Olivier ................... G16H 40/67 |

* cited by examiner

SYSTEMS AND METHODS FOR DYNAMIC RESPIRATION SENSING

CLAIM OF PRIORITY

This application claims the benefit of priority under 35 U.S.C. § 119(e) of U.S. Provisional Patent Application Ser. No. 62/621,935, filed on Jan. 25, 2018, which is herein incorporated by reference in its entirety.

TECHNICAL FIELD

This document relates generally to medical devices, and more particularly, to systems, devices and methods for monitoring patient respiration to detect a cardiopulmonary event.

BACKGROUND

Breathing is an automatic unconscious process, predominantly diaphragmatic inspiration being an active phase and expiration a passive recoil. Breathing disturbance, also known as disordered breathing, is associated with a number of pathological conditions, and may result in a variety of negative psychological, biochemical, neurological, and biomechanical influences and interferences. Patient with disordered breathing may present with hypopnea (shallow breathing), dyspnea (labored breathing), hyperpnea (deep breathing), tachypnea (rapid breathing), or a combinations of multiple breathing disorders thereof. For example, Cheyne-Stokes respiration (CSR) is a type of disordered breathing frequently observed in patients with congestive heart failure (CHF). CSR is associated with an increased risk of accelerated CHF progression is associated with rhythmic increases and decreases in tidal volume caused by alternating periods of hyperpnea followed by apnea or hypopnea.

A common symptom of CHF is dyspnea, generally refers to a sensation of shortness of breath or difficult breathing. Dyspnea may be caused by heart or lung disorders, strenuous activity, high anxiety or stress. Dyspnea derives from interactions among multiple physiological, psychological, social, and environmental factors, and may induce secondary physiological and behavioral responses. Dyspnea may be classified as chronic, acute, or terminal. Chronic dyspnea has a variable intensity and persistent shortness of breath. This is most often seen in patients with chronic obstructive pulmonary disease (COPD). Acute dyspnea causes episodes of shortness of breath with high intensity.

Another common breathing disorder is sleep apnea, prevalent in both normal and CHF populations. Sleep apnea is characterized by periods of interrupted breathing experienced during sleep. The cessation of breathing may occur repeatedly during sleep, sometimes hundreds of times a night and occasionally for a minute or longer. Sleep apnea is typically classified based on its etiology. Obstructive sleep apnea occurs when the patient's airway is obstructed by the collapse of soft tissue in the rear of the throat. Central sleep apnea is caused by a derangement of the central nervous system control of respiration. The patient ceases to breathe when control signals from the brain to the respiratory muscles are absent or interrupted. The breathing interruptions of CSR may be associated with central apnea, obstructive apnea, or mixed apnea as a combination of the central and obstructive sleep apnea. Detection of respiratory disturbances, such as Cheyne-Stokes respiration, apnea or hypopnea episodes associated with obstructive or central sleep apnea or other disordered breathing, may be useful in monitoring a patient's disease status, selecting treatment and monitoring its effectiveness.

Chronic monitoring of respiratory disturbances is also desirable in monitoring patient with other chronic diseases, such as diabetic patients. Diabetic ketoacidosis may be the first symptom to appear in a person with Type I diabetes. Persons having Type II diabetes usually develop ketoacidosis only under conditions of severe stress. Kussmaul breathing, typically characterized by relatively rapid and deep breathing, is a common symptom of ketoacidosis. Early detection and monitoring of Kussmaul breathing in diabetic patients may be valuable in monitoring diabetic status.

SUMMARY

Various types of disordered respiration may be associated with CHF. Respiratory rate is linked to patient physical condition and indicative of health state or progression of a disease. In some types of chronic diseases, changes in respiratory rate are gradual over time and may be measured over months or years. However, in worsening heart failure (WHF) such as heart failure decompensation, increases in respiratory rate can occur over days or weeks.

Rapid-shallow breathing (RSB) is a typical pattern associated with dyspnea caused by heart or lung disorders, strenuous activity, high anxiety or stress. RSB is different from tachypnea (rapid breathing) and hyperpnea (deep breathing). Tachypnea and hyperpnea can occur with hyperventilation, or over breathing beyond what is required to maintain arterial blood gases within normal limits, whereas hyperpnea may be an appropriate increase in breathing such as with exercise. RSB can be associated with symptoms of shortness of breath, or dyspnea. CHF patients frequently present with dyspnea with exertion, orthopnea (a sensation of breathlessness in a recumbent position), or paroxysmal nocturnal dyspnea (a sensation of shortness of breath that awakens the patient). Dyspnea may occur initially upon exertion, but in advanced CHF it may occur at rest, or when lying down. In diastolic heart failure, increased pressure can build up in the heart during the period of relaxation, or diastole.

Implantable medical devices (IMDs) can monitor respiration and detect cardiopulmonary events, such as events leading to WHF. An IMD may provide ambulatory respiration monitoring, which is particularly desirable for patients at risk of cardiopulmonary events. These IMDs may include or be coupled to sensors or electrodes to sense a physiologic signal, from which respiration may be sensed. However, ambulatory respiration monitoring may face a number challenges. For example, some IMDs senses respiration using an impedance signal via electrodes included in or otherwise coupled to the IMD. An IMD, such as an implantable cardiac monitor, may have a small size and slim profile. The sensed impedance signal may have weak signal strength and is prone to noises and various physiologic or non-physiologic interferences, such as motion artifacts. The impedance signal may also be affected by the device implant site and IMD orientation at the implant site. The present inventors have recognized that there remains a demand for technological solution to the technological problem of reliable ambulatory respiration sensing and accordingly, more accurate cardiopulmonary event detection, such as a WHF event.

This document discusses, among other things, a patient monitor system for ambulatory respiration monitoring. An embodiment of the system may include at least first and second sensor circuits each configured to sense a signal indicative of respiration. The signal sensed by the second senor circuit is of a different type than the signal sensed by the first sensor circuit. The system includes a respiration analyzer circuit that may select a signal from a plurality of signals of distinct types indicative of respiration including the sensed first and second signals that are respectively detected using first and second detection algorithms, and compute one or more respiration parameters from the selected signal. The respiration analyzer circuit may select or adjust a respiration detection algorithm based on a signal characteristic, such as signal quality or computational complexity, or patient conditions. The system may include a cardiopulmonary event detector to detect a cardiopulmonary event, such as a WHF event, using the computed respiration parameter.

Example 1 is a system that can sense respiration from a subject. The system comprises a respiration analyzer circuit that can receive first and second physiologic signals indicative of respiration of a subject. The second physiologic signal may be of a different type than the first physiologic signal. The respiration analyzer circuit may be configured to determine, for each of the first and second physiologic signals, at least one signal characteristic, to select a signal from the first and second physiologic signals based at least on the determined signal characteristic, and to compute a respiration parameter using the selected signal.

In Example 2, the subject matter of Example 1 optionally the respiration analyzer circuit that may be configured to receive the first physiologic signal from a first sensor circuit and the second physiologic signal from a second sensor circuit different from the first sensor circuit, and to switch from the selected first or second physiological signal to the other of the first or second physiological signal based on a change in the determined signal characteristic.

In Example 3, the subject matter of any one or more of Examples 1-2 optionally includes the respiration analyzer circuit that may configured to detect physical activity or posture of the subject, and to select the signal from the first and second physiologic signals using the detected physical activity level or posture.

In Example 4, the subject matter of any one or more of Examples 1-3 optionally includes the respiration analyzer circuit that may be configured to detect a sleep or awake state of the subject, and to select the signal from the first and second physiologic signals using the detected sleep or awake state In Example 5, the subject matter of any one or more of Examples 1-4 optionally includes the respiration analyzer circuit that may be configured to select the signal using information of time of a day when the first and second physiologic signals are sensed.

In Example 6, the subject matter of any one or more of Examples 1-5 optionally includes the signal characteristic that nay include measures of computational complexity of the first and second physiologic signals. The respiration analyzer circuit that may be configured to switch from the first physiologic signal to the second physiologic signal to compute a respiration parameter, if a respiration parameter computed using the first physiologic signal satisfies a specific condition. The second physiologic signal is different from the first physiologic signal, and is associated with more computational complexity of signal acquisition and processing than the first physiologic signal.

In Example 7, the subject matter of Example 6 optionally includes the first physiologic signal that may include an impedance signal, and the second physiologic signal that may include a motion signal. The respiration analyzer circuit may be configured to estimate a tidal volume using the impedance signal, and to switch from the impedance signal to the motion signal if the estimated tidal volume falls below a threshold.

In Example 8, the subject matter of Example 6 optionally includes the first physiologic signal that may include an impedance signal, and the second physiologic signal that may include a motion signal. The respiration analyzer circuit may be configured to determine a correlation between the impedance signal and the motion signal, and to switch from the impedance signal to the motion signal if the determined correlation falls below a threshold.

In Example 9, the subject matter of any one or more of Examples 2-8 optionally includes the first sensor circuit including an impedance sensor circuit configured to sense an impedance signal, and the second sensor circuit including an accelerometer or a gyroscope sensor circuit configured to sense a motion signal.

In Example 10, the subject matter of Example 9 optionally includes the respiration analyzer circuit that may be configured to determine an impedance vector for sensing the impedance signal based on a physical activity level or a posture of the subject.

In Example 11, the subject matter of Example 9 optionally includes the respiration analyzer circuit that may be configured to determine an accelerometer axis for sensing the motion signal based on a physical activity level or a posture of the subject.

In Example 12, the subject matter of any one or more of Examples 1-11 optionally includes a cardiopulmonary event detector configured to detect a cardiopulmonary event using the computed respiration parameter.

In Example 13, the subject matter of any one or more of Examples 1-12 optionally includes the respiration parameter that may include one or more of a respiratory rate (RR), a tidal volume (TV), a minute ventilation (MV), or a rapid shallow breathing index (RSBI), or a trend of one or more of the RR, TV, MV, or RSBI.

In Example 14, the subject matter of any one or more of Examples 1-13 optionally includes the first physiologic signal that is detected using a first detection algorithm, and the second physiologic signal that is detected using a second detection algorithm.

In Example 15, the subject matter of Example 14 optionally includes a respiration sensor that may be configured to sense the first physiologic signal using the first detection algorithm, and to sense the second physiologic signal using the second detection algorithm. The first detection algorithm has a different computational complexity than the second detection algorithm.

In Example 16, the subject matter of Example 15 optionally includes the respiration analyzer circuit that may be configured to switch from a first respiration detection algorithm to a second respiration detection algorithm different from the first respiration detection algorithm based at least on the determined signal characteristic. The first and second respiration detection algorithms may each be selected from the plurality of candidate detection algorithms including two or more of a peak detector, a zero-crossing detector, a correlator, or a frequency analyzer.

Example 17 is a method for sensing respiration from a subject via a medical system. The method comprises steps of: sensing from the subject first and second physiologic signals using at least one sensor circuit, the first and second physiologic signals indicative of respiration and being of different types from each other; determining, for each of the first and second physiologic signals, at least one signal characteristic; selecting a signal from the first and second physiologic signals using a respiration analyzer circuit based at least on the determined signal characteristic; and computing, via the respiration analyzer circuit, a respiration parameter using the selected signal.

In Example 18, the subject matter of Example 17 optionally includes detecting a patient functional state including one or more of physical activity, posture, or sleep or awake state of the subject. Selection of the signal from the first and second physiologic signals may be based on the detected patient functional state.

In Example 19, the subject matter of Example 17 optionally includes the signal characteristic that may include measures of computational complexity of the first and second physiologic signals. The method may include a step of switching from the first physiologic signal to the second physiologic signal if a respiration parameter computed using the first physiologic signal satisfies a specific condition. The second physiologic signal differs from the first physiologic signal, and is associated with more computational complexity of signal acquisition and processing than the first physiologic signal. The method includes computing the respiration parameter using the second physiologic signal.

In Example 20, the subject matter of Example 19 optionally includes the first physiologic signal that may include an impedance signal, and the second physiologic signal that may include a motion signal. The method further comprises steps of determining a correlation between the impedance signal and the motion signal, and switching from the impedance signal to the motion signal if the determined correlation falls below a threshold.

In Example 21, the subject matter of Example 17 optionally includes the first physiologic signal that may be detected using a first detection algorithm, and the second physiologic signal that may be detected using a second detection algorithm.

In Example 22, the subject matter of Example 17 optionally includes detecting a cardiopulmonary event using the computed respiration parameter.

Various embodiments described herein can improve the medical technology of device-based, computerized, respiration monitoring and disordered breathing detection. Breathing disturbances may be associated with a disease condition, such as WHF, sleep apnea, or other various cardiac, pulmonary, neurological, or psychological disorders. Monitoring respiratory disturbances may provide useful clinical diagnostic or prognostic information, or trigger other types of patient monitoring or delivery of desired therapies. As discussed above, conventional ambulatory respiration detection faces a challenge of low signal quality or interferences. Systems and methods discussed in this document provide a technological solution by using a dynamic respiration-sensing paradigm, including selection and switching among sensors, sensing modalities, or respiration detection algorithms, to accommodate different or changing patient conditions and/or environmental conditions. The flexibility provided by the dynamic respiration sensing discussed herein may improve the accuracy and reliability of detection and characterization of breathing disorders. Accordingly, therapies may be more timely provided or adjusted (e.g., ambulatory therapy such as cardiac pacing), hospitalization may be reduced, and healthcare costs associated with patient management may be reduced.

The dynamic respiration sensing discussed in this document may also improve functionality of an ambulatory device such as an IMD. The dynamic respiration sensing allows for more efficient device memory usage for storing the sensor signal more reflective of patient respiration changes under various patient conditions. More accurate respiration sensing may also help reduce false positive cardiopulmonary event detection, and fewer therapy interventions may be required. Accordingly, battery life and device longevity of an IMD may be extended. Furthermore, fewer unnecessary drugs and procedures may be scheduled, prescribed, or provided; and overall system cost savings associates with patient management may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for sensing respiration from a subject. An embodiment of a respiration monitoring system may include a respiration analyzer circuit to select a physiologic signal from a plurality of physiologic signals of distinct types indicative of respiration, such as sensed using physiologic sensors. The respiration analyzer circuit can compute one or more respiration parameters using the selected signal. The system may select or adjust a respiration detection algorithm for detecting the respiration parameters. The physiologic signal or the respiration detection algorithm may each be selected based on a signal characteristic such as signal quality measure or computational complexity measure, or a patient condition. A cardiopulmonary event such as a WHF event may be detected using the respiration parameters.

Figure 1:
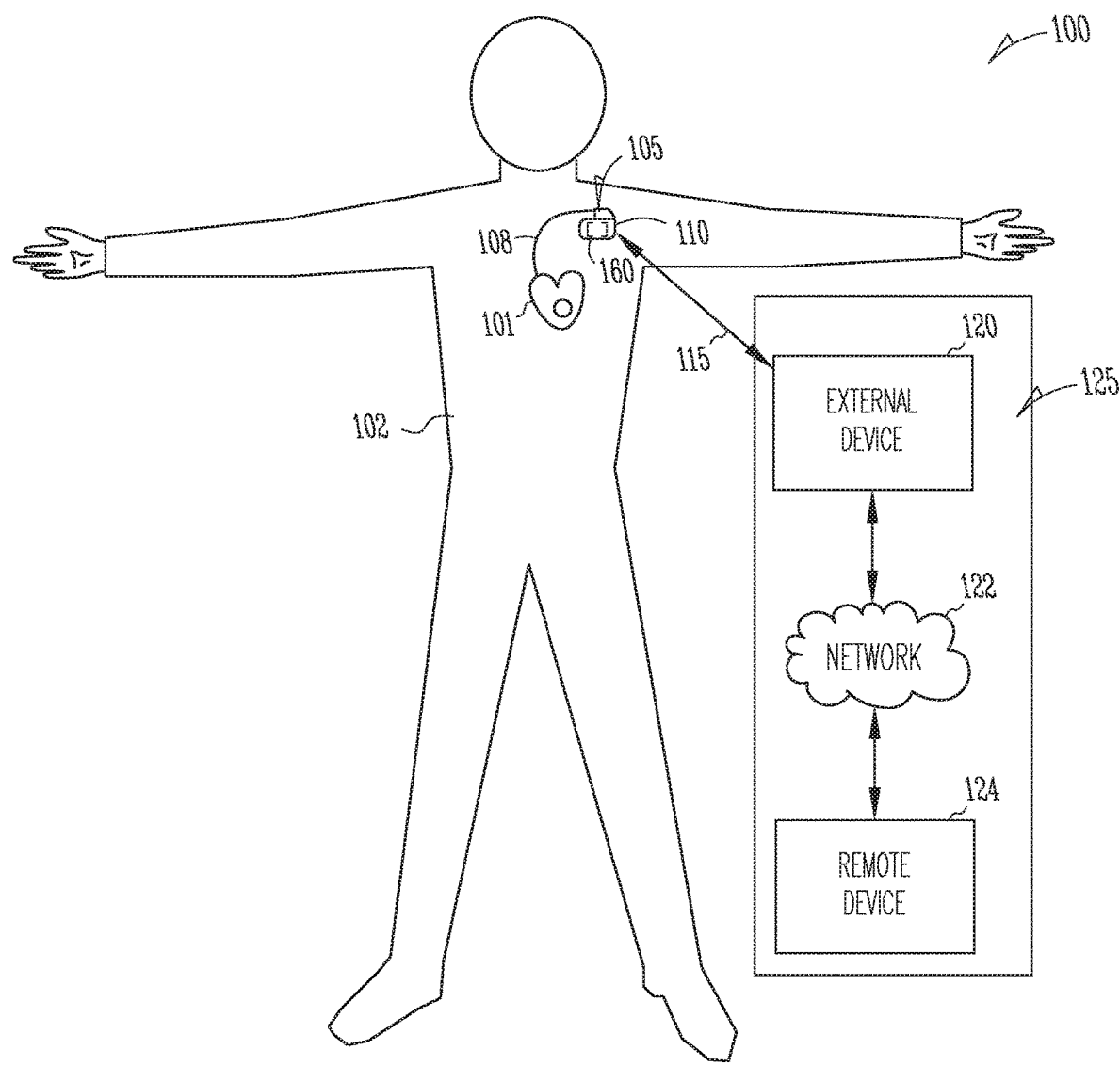
FIG. 1 illustrates generally an example of a patient monitor system and portions of an environment in which the system may operate.

FIG. 1 illustrates generally an example of a patient monitor system 100 and portions of an environment in which the system 100 may operate. The patient monitor system 100 may chronically monitor a patient 102 to assess patient risk of developing WHF. Portions of the system 100 may be ambulatory. Portions of the system 100 may be disposed in a patient home or office, a hospital, a clinic, or a physician's office.

As illustrated in FIG. 1, the patient monitor system 100 may include an ambulatory system 105 associated with the patient 102, an external system 125, and a telemetry link 115 providing for communication between the ambulatory system 105 and the external system 125. The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as ambulatory cardiac monitors (ACMs) or loop recorders, or patient monitors, among others. The AMD 110 may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example and not limitation, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110. In an example, one or more sensors or sensing electrodes may be enclosed within or attached to the ambulatory system 105.

The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. The physiologic signals may contain information about patient respiration, or otherwise be modulated by respiration. Examples of the physiologic signal may include one or more of electrocardiogram, intracardiac electrogram, arrhythmia, heart rate, heart rate variability, tissue impedance, thoracic impedance, cardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiratory rate, tidal volume, respiratory sounds, body weight, or body temperature.

The AMD 110 may include a respiration detector circuit 160 configured to detect respiration and compute one or more respiration parameters, such as a respiratory cycle, an inspiration phase or an expiration phase, a respiratory rate, a tidal volume, or a minute ventilation, among others. The respiration detector circuit 160 may include two or more sensor circuits each coupled to a physiologic sensor to sense a distinct type of signal indicative of respiration. The respiration detector circuit 160 may select at least one signal from a plurality of physiologic signals of distinct types, such as sensed by various sensors, based on signal qualities, patient conditions, sensor configurations, or environmental conditions, among others. The respiration detector circuit 160 may detect respiration and compute one or more respiration parameters using the selected signal. The respiration detector may select or adjust a respiration detection algorithm for detecting the respiration parameters. The detection algorithm may be selected or adjusted according to a signal characteristic such as signal quality measure or computational complexity measure, or a patient condition. The AMD 110 may include circuitry that detect a cardiopulmonary event using the detected respiration parameters, such as a WHF event, a sleep apnea event, or other medical conditions presented with breathing disturbances or disordered breathing.

The AMD 110 may include a therapy unit that may generate and deliver a therapy to the patient. The therapy may be initiated or modified in response to the detection of the cardiopulmonary event. In some examples, the therapy may be initiated or modified in response to a change in respiration pattern. The therapy may be preventive or therapeutic in nature, and may modify, restore, or improve patient health state. Examples of the therapy may include electrical, magnetic, or other forms of therapy. In some examples, the AMD 110 may include a drug delivery system such as a drug infusion pump device to deliver drug therapy to the patient. In various examples, the AMD 110 may monitor patient physiologic responses to the delivered therapy to assess the efficacy of the therapy.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect respiration and cardiopulmonary event, or optionally delivering or adjusting a therapy to the patient 102. The external system 125 may communicate with the AMD 110 via the communication link 115. The device data received by the external system 125 may include real-time or stored physiologic data from the patient 102, diagnostic data, responses to therapies delivered to the patient 102, or device operational status of the AMD 110 (e.g., battery status and lead impedance). The communication link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi- or distributed computing and processing system. In an example, the remote device 124 may include a data processor configured to perform heart failure detection or risk stratification using the physiologic data received from the AMD 110. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the detection respiration parameters and/or cardiopulmonary events to a system user, such as a clinician. The external device 120 or the remote device 124 may include respective display for displaying the physiologic data acquired by the AMD 110. The physiologic data may be presented in a table, a chart, a diagram, or any other types of textual, tabular, or graphical presentation formats. The external device 120 or the remote device 124 may include a printer for printing hard copies of signals and information related to the cardiopulmonary event. The presentation of the output information may include audio or other media formats. In an example, the output unit 254 may generate alerts, alarms, emergency calls, or other forms of warnings to signal the system user about the cardiopulmonary event. The clinician may review, perform further analysis, or adjudicate the respiration detection. The detected respiration parameters and cardiopulmonary events, optionally along with the data acquired by the AMD 110 and other sensors or devices, may be output to a process such as an instance of a computer program executable in a microprocessor. In an example, the process may include an automated generation of recommendations for initiating or adjusting a therapy, or a recommendation for further diagnostic test or treatment.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
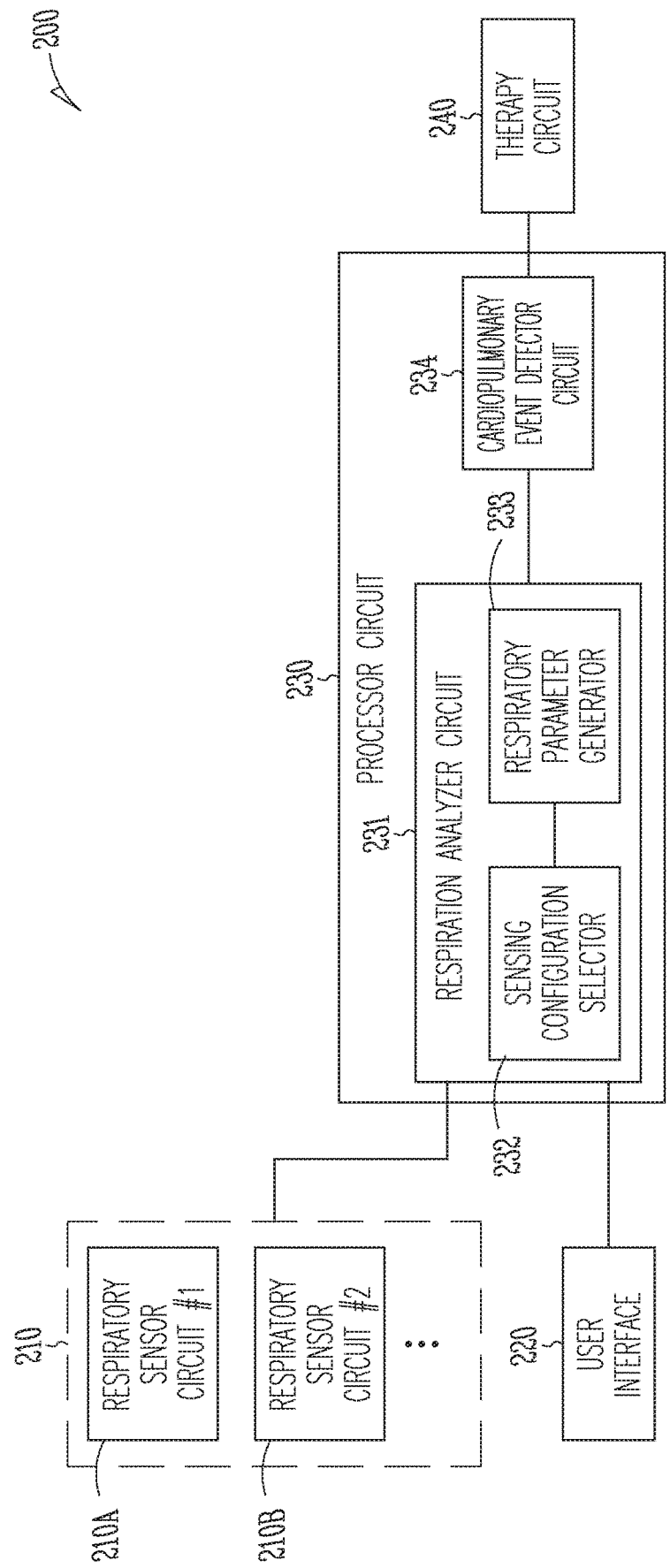
FIG. 2 illustrates generally an example of a cardiopulmonary event detector system.

FIG. 2 illustrates generally an example of a cardiopulmonary event detector system 200 to detect a cardiopulmonary event in a subject. At least a portion of the cardiopulmonary event detector system 200 may be implemented in the AMD 110, the external system 125 such as one or more of the external device 120 or the remote device 124, or distributed between the AMD 110 and the external system 125. The cardiopulmonary event detector system 200 may include sensor circuitry 210, a user interface 220, a processor circuit 230 for detecting respiration parameters and further detecting a cardiopulmonary event, and an optional therapy circuit 240 for delivering a therapy.

The sensor circuitry 210 may include a sense amplifier circuit to sense at least one physiologic signal from a subject. The sensor circuitry 210 may be coupled to an implantable, wearable, or otherwise ambulatory sensor or electrodes associated with the subject. The sensor may be incorporated into, or otherwise associated with an ambulatory device such as the AMD 110. The sensed physiologic signal may be indicative of respiration, such as a physiologic signal modulated by respiration. Examples of the physiologic signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, a thoracic or cardiac impedance signal, a motion signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, a physiologic response to activity, among others. In some examples, the physiologic signals sensed from a patient may be stored in a storage device, such as an electronic medical record system, and the sensor circuitry 210 may be configured to receive a stored physiologic signal from the storage device in response to a user input or triggered by a specific event.

The sensor circuitry 210 includes two or more respiratory sensor circuits 210A, 210B, etc., each of which is configured to sense a distinct physiologic signal indicative of respiration. Each of the respiratory sensor circuits in the sensor circuitry 210 may be coupled to an implantable, wearable, holdable, or other ambulatory respiratory sensors configured to sense, directly or indirectly, airflow or lung volume change during respiratory cycles. The respiratory sensor circuits may each include sub-circuits to digitize, filter, or perform other signal conditioning operations on the sensed physiologic signal. In an example, the respiratory sensor circuits in the sensor circuitry 210 may be included in one medical device, such as the AMD 110. In another example, the respiratory sensor circuits may be distributed between two or more devices. For example, the respiratory sensor circuit 210A may be included in a first device (e.g., a pacemaker or a cardiac resynchronization device), and the respiratory sensor circuit 210B may be included in a subcutaneously implantable cardiac monitor in communication with the first device.

In an example, one of the respiratory sensor circuits (e.g., respiratory sensor circuit 210A) is configured to sense impedance via electrodes attached to or implanted in the patient. An example of the sensed impedance includes a thoracic impedance representing an electrical property of the chest and varies during inspiration expiration phases, such that the impedance increases during inspiration and decreases during expiration. Electrical current may be injected into a body part (e.g., the chest) between two stimulation electrodes to establish an electric field that covers at least a portion of the chest, and voltage drop may be measured between a pair of sensing electrodes. The impedance may be determined using Ohm's law.

The impedance-sensing electrodes may be associated with an implantable lead coupled to an implantable medical device. By way of example and not limitation, impedance may be measured between an electrode on a right ventricular and the can housing of the implantable device implanted at a pectoral region, between an electrode on a left ventricle and the can housing of the implantable device, or between a right atrium electrode and the can housing of the implantable device. Alternatively, impedance-sensing electrodes may be included within or on an ambulatory physiologic monitor, such as an implantable cardiac monitor. The impedance vector, such as defined by a pair of voltage-sensing electrodes, may be constrained by the size and shape of the implantable cardiac monitor. In an example, the implantable cardiac monitor has a small size and slim profile. Accordingly, the impedance vector may be a small vector characterized by relative short spacing between the voltage-sensing electrodes and covers a small portion of the chest. The small vector impedance may be sensitive to implant site location and orientation of the implantable cardiac monitor. In some examples, impedance may be measured using non-invasive surface electrodes removably attached to a patient chest.

In an example, one of the respiratory sensor circuits (e.g., respiratory sensor circuit 210B) is configured to sense motion via an accelerometer sensor attached to or implanted in the patient, such as on the patient chest. An example of the motion signal includes a chest wall motion representing chest expansion and contraction induced by respiration, which generates forces detectable by an accelerometer. The accelerometer may include a single-axis to sense chest wall motion in one direction, or a multi-axis accelerometer to sense chest wall motion at two or more directions. Examples of the accelerometers may include a piezoelectric accelerometer such as one employing piezoelectric crystals, a capacitive accelerometer, a strain gauge accelerometer, or a Hall-effect accelerometer that senses a change in magnetic field, or various micro-machined micro-electromechanical systems (MEMS) accelerometers, among others. Additionally or alternatively, one of the respiratory sensor circuits may sense motion via a gyrometer or gyroscope (e.g., a one-, two-, or three-axis gyroscope), a pressure sensor, a magnetometer (e.g., a compass), an inclinometer, a sensing fabric, a force sensor, a strain gauge, an electromyography (EMG) sensor, among other sensors for motion detection.

Although chest wall motion is discussed in this document for respiration sensing, this is meant to be illustrative rather than restrictive in nature or limiting in any way. Motion of other body parts may also be indicative of respiration. In various examples, one or more of the sensors discussed herein may be configured for placement on the abdomen or other body parts other than the chest to sense respiration.

In some examples, the sensor circuitry 210 may include, for example, a respiration sensor circuit coupled to a flowmeter that directly senses airflow in the respiratory system or volume change in the lungs. In another example, respiration may be sensed using one or more of a strain sensor configured to sense changes in chest muscle tension corresponding to respiration cycles, an accelerometer to measure acceleration associated with displacement or movement of chest walls corresponding to respiration, or an acoustic sensor to sense cardiac acoustic signal that is modulated by respiration. In yet another example, respiration may be extracted from a cardiac electrical signal modulated by respiratory signal, such as an ECG signal. During inspiration, the diaphragm shift downwards away from the apex of the heart. The increased filling of the lungs further stretches the apex of the heart towards the abdomen. During expiration, the lung volume reduces, and the diaphragm elevates upwards toward the heart, which compresses the apex of the heart towards the breast. As a result, the angle of the electric cardiac vector that gives rise to the ECG signal changes during inspiration and respiratory phases, which leads to cyclic variation in R-wave amplitude on the ECG signal. The respiratory signal can be obtained from the R-wave amplitude signal using demodulation method, such as by filtering an R-wave amplitude trend through a low-pass filter or a bandpass filter. Other respiratory sensors may alternatively include patient-external respiratory bands, implantable or patient-external breath sound detector, blood oxygen detector, and other sensors configured to sense a respiration-modulated physiologic signal, which can be found in Lee et al., U.S. Pat. No. 7,678,061 entitled "System and method for characterizing patient respiration", filed on Apr. 15, 2004, which is incorporated herein by reference in its entirety.

The user interface 220 may include a display screen and an input device. The display screen may be configured to display sensed physiologic signals, cardiopulmonary events detected by the system, other patient physiologic information, or parameters pertaining to system or device functionality or operating status. The input device may include a keyboard, an on-screen keyboard, a mouse, a trackball, a touchpad, a touch-screen, or other pointing or navigating devices. A user may use the input device to program one or more parameters for a system component, such as the sensor circuitry 210, the respiration analyzer circuit 231, the cardiopulmonary event detector circuit 234, or the therapy circuit 240. In an example, through the input device, the user may select one or more respiratory sensors, or to confirm, reject, or modify system-generated selection of respiratory sensors. The user may use the input device to select, confirm, or modify a system-generated detection algorithm for detecting one or more respiration parameter.

The processor circuit 230 may generate respiratory diagnostics, and detect a cardiopulmonary event. The processor circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 230 may include circuit sets comprising one or more other circuits or sub-circuits, including a respiration analyzer circuit 231 and a cardiopulmonary event detector circuit 234. These circuits or sub-circuits may, either individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The respiration analyzer circuit 231 may include sub-circuits, including a sensing configuration selector 232 and a respiratory parameter generator circuit 233. The sensing configuration selector 232 may select or adjust a respiration-sensing configuration. In an example, the sensing configuration selector 232 may select at least one physiologic signal from a plurality of physiologic signals of distinct types and indicative of respiration, such as sensed by the respiratory sensors circuits 210A, 201B, etc. The selection may be based on a signal characteristic, such as signal quality measure or computational complexity measure, patient conditions such as patient functional states, sensor configurations, or environmental conditions, among others. In another example, the sensing configuration selector 232 may select a sensor operation mode, such as a particular impedance vector out of a plurality of candidate vectors for sensing impedance or a particular axis of a multi-axis accelerometer for sensing motion. Examples of respiration sensing configuration selection are discussed below, such as with reference to FIGS. 3-5.

The sensing configuration selector 232 may select or adjust a respiration detection algorithm for detecting respiration. The selection of the respiration detection algorithm may be based on a signal characteristic such as signal qualities, patient conditions, sensor configurations, environmental conditions, or a computational cost, among others. In one example, the sensing configuration selector 232 may quantify signal changes caused by respiration and select a respiration detection algorithm based on the signal changes. In another example, the sensing configuration selector 232 may quantify both the signal changes caused by respiration and noise levels on the signal and select a respiration detection algorithm based on both the signal changes and the noise levels. By way of example and not limitation, respirator rate may be detected using one of a plurality of candidate algorithms including, for example, a peak detector, a zero-crossing detector, a correlator, or a frequency analyzer. The peak detector detects positive or negative peaks in a physiologic signal indicative of respiration, and determines the respiratory rate using time intervals between the detected peaks. For example, a positive impedance peak represents an end of inspiration when the impedance reaches its maximum during a respiratory cycle; and a negative impedance peak represents an end of expiration when the impedance reaches its minimum during a respiratory cycle. The zero-crossing detector detects when a physiologic signal indicative of respiration crosses signal baseline (denoted by "zero") representing a DC component of the physiologic signal during the inspiration phase and the expiration phase of a respiratory cycle. The respiratory rate may be determined using the timing of the zero-crossings. The correlator detects respiratory rate using an autocorrelation of a physiologic signal indicative of respiration. As the peaks of the autocorrelation signal represent periodicity of respiration, the respiratory rate may be determined based on a time interval between adjacent autocorrelation peaks. The correlator may alternatively detect respiratory rate using a cross-correlation between a physiologic signal indicative of respiration and a respiration template that includes one or more respiratory cycles under a controlled condition, such as when the subject is physically inactive or maintains at a specific posture. Respiratory cycles may be detected such as based on the peak of cross-correlation, and the respiratory rate may be derived from the detected respiratory cycles. The frequency analyzer involves frequency analysis or spectral analysis, such as based on a Fourier transform of the physiologic signal. Signal peak or the spectral peak in the frequency domain may correspond to the periodicity of the respiration, and the respiratory rate may be derived from the frequency at which the signal peak or spectral peak occurs.

The respiratory parameter generator 233 may compute one or more respiration parameters from the selected one or more physiologic signals. The respiration parameters may be generated using a plurality of detection algorithms. In an example, the respiratory parameter generator 233 may compute one or more respiration parameters using the respiration detection algorithm selected or adjusted by the sensing configuration selector 232 as previously discussed. By way of example, the respiration parameters may include respiratory cycles, respiratory cycle period or respiratory rate, a tidal volume, a minute ventilation, a respiratory sound characteristic (such as a characteristic frequency of respiratory sound), or respiratory phase such as inspiration phase and expiration phase. The inspiration phase is a period between an end-of-expiration state and the next end-of-inspiration state. The expiration phase is a period between an end-of-inspiration state and the next end-of-expiration state. In an example where the respiratory sensor directly or indirectly measures the lung volume, the end-of-expiration state may correspond to the minimal lung volume within a specified detection window; and the end-of-inspiration state may correspond to the maximal lung volume with a specified detection window. In another example where the respiratory sensor senses impedance, the impedance increases when the air volume in the lungs increases. The end-of-expiration state may correspond to the minimal impedance within a specified detection window; and the end-of-inspiration state may correspond to the maximal impedance within a specified detection window. In some examples, the generated respiration parameters may include a respiratory pattern, such as a rapid-shallow breathing index (RSBI) (represented by a ratio of a respiratory rate measurement to a tidal volume measurement), Cheyne-Stokes pattern, cluster breathing, Kussmaul's breathing, apneustic breathing, or ataxic breathing, among other patterns.

The cardiopulmonary event detector circuit 234 may detect a cardiopulmonary event using the computed respiration parameter. By way of example and not limitation, the cardiopulmonary event may include CHF, pulmonary edema, sleep apnea, COPD, asthma, pulmonary embolism, or breathing disturbance or disorders associated with other medical conditions such as diabetic ketoacidosis. In an example, the cardiopulmonary event detector circuit 234 may include a trending circuit to generate one or more respiration parameter trends, such as a respiratory rate trend (RRT), a tidal volume trend, a minute ventilation trend, or an RSBI trend, among other respiration parameter trends. The cardiopulmonary event detector circuit 234 may detect a cardiopulmonary event if one or more of the respiration parameter trends satisfy respective conditions, such as exceeding a threshold, or falling within a specific value range. In some examples, the cardiopulmonary event detector circuit 234 may generate a composite respiratory index using the respiration parameter trends, such as a weighted combination of two or more of the respiration parameter trends, and detect a cardiopulmonary event if the composite respiratory index satisfies a specific condition. The weight factors may be determined based on performance of the respiratory parameter trend in detecting the cardiopulmonary event. The weight factors may also be determined using patient population data. The cardiopulmonary event detector circuit 234 may additionally or alternatively use the one or more respiration parameter trends to predict a patient risk of experiencing a specific cardiopulmonary event in the future.

The optional therapy circuit 240 may deliver a therapy to the patient. The therapy may be delivered in response to the detection of a cardiopulmonary event. In some examples, the therapy circuit 240 may modify an existing therapy, such as adjust a stimulation parameter (e.g., cardiac pacing rate or pacing mode) or drug dosage. Examples of the therapy may include electrostimulation therapy delivered to the heart, a nerve tissue, or other target tissue, a cardioversion therapy, a defibrillation therapy, or drug therapy. In an example, the cardiopulmonary event detector circuit may generate a worsening heart failure (WHF) risk indicator using at least the respiration parameters. Many physiologic signals or signal metrics may be selected based on the WHF risk indicator, and used to detect a WHF event. The therapy circuit 240 may initiate or modify delivery of a heart failure therapy in response to the detection of WHF event.

Figure 3:
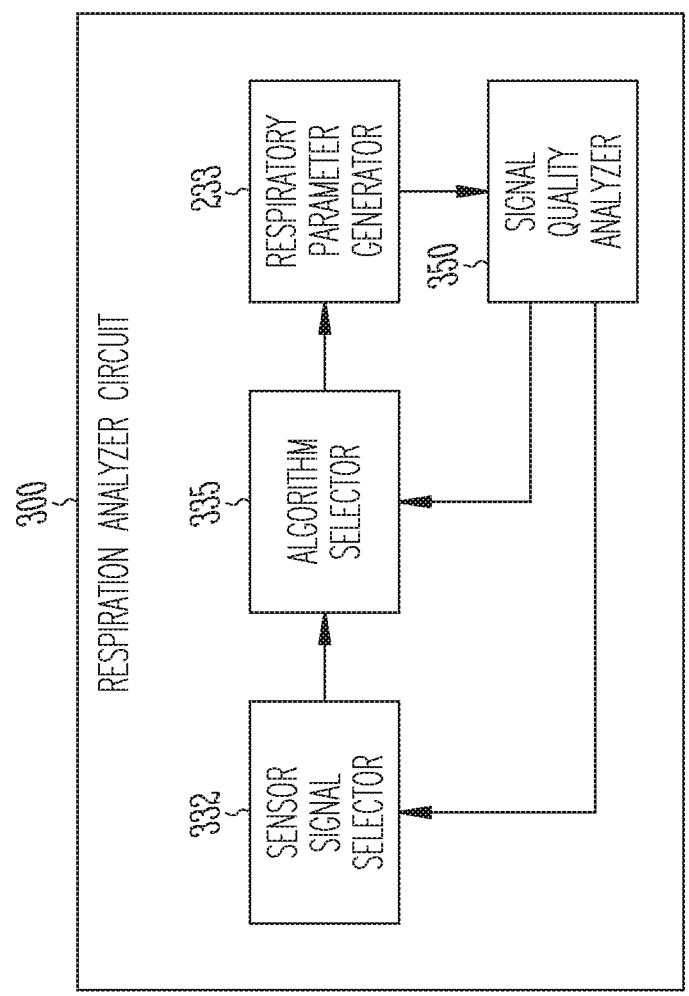
FIG. 3 illustrates generally an example of respiration analyzer circuit, which is an embodiment of a portion of a cardiopulmonary event detector system.

FIG. 3 illustrates generally an example of respiration analyzer circuit 300, which may be an embodiment of the respiration analyzer circuit 231 of the cardiopulmonary event detector system 200. The respiration analyzer circuit 300 may include one or more of a sensor signal selector 332, an algorithm selector 335, a respiratory parameter generator 233, and a signal quality analyzer 350. The sensor signal selector 332 and the algorithm selector 335 are each embodiments of the sensing configuration selector 232. The sensor signal selector 332 may select a physiologic signal from a plurality of physiologic signals of different types and indicative of respiration, such as sensed by the respiratory sensors circuits in the sensing circuitry 210. In an example, a physiologic signal may initially be selected based on signal quality, such that a physiologic signal with stronger signal intensity or a higher signal-to-noise ratio (SNR) may be selected. In another example, initial physiologic signal selection may be based on computational cost associated with signal acquisition and processing, including power consumption, data rate requirement, complexity of data processing, data storage requirement, or bandwidth requirement for data communication between devices, among others. The computational cost can be a measure of system or device resources allocated for performing data collection, processing, storage, or communication, among other operations. The sensor signal selector 332 may initially select a physiologic signal with lower computational cost, such as one requiring less power, less complex hardware support, or fewer system resources. For example, between an impedance signal sensed using an impedance sensor circuit and a motion signal sensed using an accelerometer, the sensor signal selector 332 may initially select impedance signal at least due to its relatively lower power consumption in operation.

In some examples, the initial physiologic signal selection may be based on a balance between a detection performance and a computational cost. The detection performance is related to the signal quality of the physiologic signal, and may be characterized by an accuracy rate of detecting respiration or a cardiopulmonary event under various patient or environmental conditions. The balance may be assessed using a cost-effectiveness metric, such as a linear or nonlinear combination of the gain achieved with a particular physiologic signal (e.g., the accuracy rate of detecting respiration or cardiopulmonary event under various conditions), and the cost associated with data acquisition and processing of a particular physiologic signal. The cost may additionally include cost associated with frequent switching among different physiologic signals for sensing respiration. For example, switching from one physiologic signal (e.g., chest wall motion) to another (e.g., thoracic impedance) requires activation or deactivation of different sensor circuits, and adjustment of sensing modalities and gain factors. This may have a negative impact on the continuity or consistency of the resultant respiration signal, which constitutes additional cost. By way of example and not limitation, the balance may be expressed as a cost-to-gain ratio for a particular physiologic signal. For example, the motion signal sensed by an accelerometer may have a higher accuracy in detecting respiration at a higher cost of computational complexity and power requirement. In contrast, the impedance may require lower computational cost and less system resource (such as lower computational complexity involved in data collection, processing, storage, or communication), but may present with weak signal strength such as due to a small impedance vector with relatively short inter-electrode spacing and/or a particular impedance vector direction. The sensor signal selector 332 may select, between the impedance signal and the accelerometer signal indicative of motion, one associated with a lower cost-to-gain ratio.

For the selected physiologic signal, the algorithm selector 335 may select or adjust a respiration detection algorithm for detecting respiration and computing one or more respiration parameters from the selected physiologic signal. In an example, the respiration detection algorithm may be selected according to a computational cost required for computing a respiration parameter. For example, in detecting respiratory rate, the algorithm selector 335 may initially select a zero-crossing detector over a correlator or a frequency analyzer, due to the less computation involved in zero-crossing method.

The respiratory parameter generator 233 may apply the selected detection algorithm to the selected signal, and compute one or more respiration parameters. The signal quality analyzer 350 may be coupled to the respiratory parameter generator 233, and generate an indication of signal quality of the respiration parameter. Examples of the signal quality indication may include an SNR, or a signal intensity measure. The signal qualify of a respiration parameter may be affected by factors including a sensor dynamic range, amplification and pre-processing configuration, or sensor location such as an implantation site of an implantable physiologic monitor, among others. Depending on the signal quality indication, the sensor signal selector 332 may dynamically switch to a different physiologic signal than the originally selected physiologic signal. In an example, the signal quality analyzer 350 may determine the SNR of a respiration parameter (e.g., a ventilation period, which represents duration of a respiratory cycle) using a root-mean-squared (RMS) value of impedance-based respiration parameter estimates and a RMS value of the noise presented in the impedance signal. If the SNR falls below a threshold, or if the RMS of the noise exceeds a noise threshold, then the sensor signal selector 332 may switch to a different physiologic signal, such as a chest wall motion or abdomen motion signal sensed by an accelerometer. In another example, the signal quality analyzer 350 may determine signal strength of an impedance-based respiration parameter, such a peak-to-peak impedance value. The peak-to-peak impedance represents a maximum impedance change within a respiratory cycle, which correlates to a tidal volume. If the impedance signal strength (e.g., peak-to-peak value) falls below a threshold indicating a reduced tidal volume, then the sensor signal selector 332 may dynamically switch to a different physiologic signal, such as a chest wall motion signal or an abdomen motion signal.

Additionally or alternatively, the algorithm selector 335 may dynamically switch to a different detection algorithm than the originally selected detection algorithm based on the signal quality indication. In an example, if the respirator rate detected using the zero-crossing detector or peak detector has a poor quality (e.g., large variability of the respiratory rate estimates, or substantial failure rate in detecting the peaks or zero-crossings such as due to high physical activity level), then the algorithm selector 335 may switch to a different detection algorithm, such as correlator or a frequency analyzer or other computationally more intensive algorithm.

Figure 4:
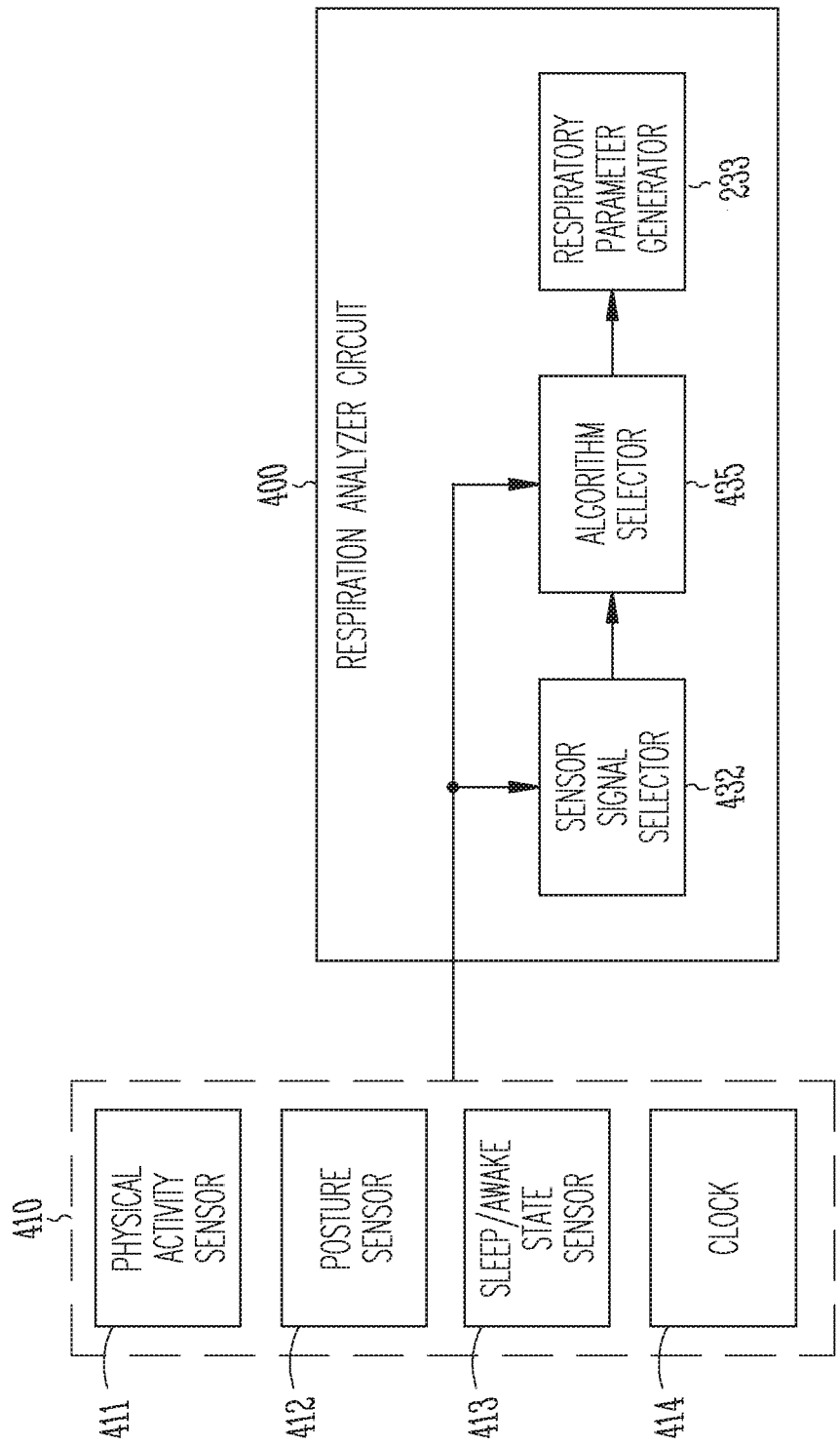
FIG. 4 illustrates generally another example of a respiration analyzer circuit.

FIG. 4 illustrates generally an example of respiration analyzer circuit 400, which may be an embodiment of the respiration analyzer circuit 231 of the cardiopulmonary event detector system 200. The respiration analyzer circuit 400 may include one or more of a sensor signal selector 432, an algorithm selector 435, and a respiratory parameter generator 233. The respiration analyzer circuit 400 may be coupled to one or more sensor circuits 410 each configured to detect patient conditions, such as functional states. By way of example and not limitation, and as illustrated in FIG. 4, the sensor circuits 410 may include a physical activity sensor 411, a posture sensor 412, a sleep/awake state sensor 413, or a clock 414 to indicate time of day. The physical activity sensor 411 may be an ambulatory sensor for sensing intensity, duration, or a pattern of physical activity. The physical activity sensor may include a single-axis or a multi-axis accelerometer. The strength of the acceleration signal may be indicative of physical activity level. In an example, the acceleration signal may be full-wave rectified, and average over a specified time period to produce a metric characterizing a physical activity level. The posture sensor 412 may be an ambulatory sensor, such as a tilt switch, an accelerometer, or an impedance sensor configured to detect posture or position. In an example, posture can be represented by a tilt angle sensed by a tilt switch. The sleep/awake sensor 413 may include accelerometers, piezoelectric sensors, biopotential electrodes and sensors, or other physiologic sensors. These sensors may detect sleep states through brain activities such as via electroencephalograms (EEG), or systematic responses indicative of sleep states such as position, frequency of change of posture, intensity of activity, respiration, heart rate, or other physiologic signal signals. In some examples, information of physical activity, posture, sleep/awake state may be derived using different signal processing (e.g., signal filters with distinct pass bands and gains) of a physiologic signal acquired using one sensor, such as an accelerometer sensor. The clock 414 may detect time of a day, such as a daytime or a nighttime of a day. The time of day may indirectly indicate patient physical activity levels, posture, or asleep/awake state, such as according to patient daily routine.

Information about one or more of physical activity, posture, sleep/awake state, or time of a day may be used for selecting a physiologic signal or for selecting a detection algorithm to detect respiration and to generate one or more respiration parameters. For example, motion sensed by an accelerometer may be more susceptible to interferences when the patient is physically active than an impedance signal. The sensor signal selector 432 may select the impedance signal if the physical activity intensity or duration exceeds a respective threshold, or when a particular activity pattern such as one indicating repetitive body motion is detected. The sensor signal selector 432 may dynamically switch to motion signal when the physical activity intensity or duration falls below respective threshold indicative of a low activity level. In another example, the sensor signal selector 432 may select the motion signal if the posture sensor 412 detects a supine or a sitting posture, and switch to impedance signal when a posture change to a standing position is detected. In another example, the sensor signal selector 432 may select the motion signal if the sleep/awake state sensor 413 detects a sleep state, and switch to the impedance signal when a transition to awake state is detected. In yet another example, the sensor signal selector 432 may select the motion signal during a particular time of day as indicated by the clock 414, such as during a nighttime or a specified time period when the patient is likely physically inactive, in a sitting or supine position, or during asleep. The sensor signal selector 432 may switch to the impedance signal when the clock 414 indicates daytime or a specified time period during a day when the patient is likely physically active, in a sitting or supine position, or in a sleep state.

In various examples, the sensor signal selector 432 may select a sensor configuration for sensing a physiologic signal. The sensor configuration may include information of sensor location, such as an implant site for an implantable physiologic monitor configured to monitor respiration, among other physiologic parameters. In an example, impedance may be sensed using various impedance vectors. Both the direction of the impedance vector and the spacing between sensing electrodes (e.g., voltage-sensing electrodes) in the electrical field may affect impedance measurements. Additionally, at least due to the differences in impedance orientation and inter-electrode distance, some impedance vectors are more sensitive to posture or physical activity than other impedance vectors. The sensor signal selector 432 may select an impedance vector that is less prone to patient posture or physical activity for detecting respiration parameters. In another example, motion may be sensed using a multi-axis accelerometer that can provide motion information along multiple directions. Depending on the mode of activity or posture, one accelerometer axis may be more sensitive to posture or physical activity, and thus more likely introduce interferences to the motion signal than other impedance vectors. The sensor signal selector 432 may select an accelerometer axis that is less prone to patient posture or physical activity for detecting respiration parameters.

The algorithm selector 435 may select an algorithm from a plurality of candidate algorithms using one or more of patient physical activity, posture, sleep/awake state, or the time of day information, such as provided respectively for the physical activity sensor 411, the posture sensor 412, the sleep/awake state sensor 413, or the clock 414. For example, in detecting respiratory rate, a peak detector or a zero-crossing detector may be computationally less costly, but more susceptible to interferences such as when the patient is physically active, than a correlator or a frequency analyzer. The algorithm selector 435 may select the peak detector or the zero-crossing detector to detect respiratory rate if one or more of the sensors 411-414 indicate that the patient is physically inactive, in a sitting or supine position, in a sleep state, or during a nighttime. If one or more of the sensors 411-414 indicate that the patient becomes physically active, in a standing position, in an awake state, or during a daytime, then the algorithm selector 435 may switch to the correlator or the frequency analyzer, or other computationally more costly but more robust algorithms.

In various examples, one or more of the physical activity sensor 411, the posture sensor 412, the sleep/awake state sensor 413, or the clock 414 may continuously or periodically detect patient physical activity, posture, sleep or awake state, or time of day, respectively. When a change of patient functional state is detected (e.g., a different physical activity level, duration, or pattern, or a different posture, or a transition from a sleep state to an awake state or vice versa), the sensor signal selector 432 and the algorithm selector 435 may dynamically switch to a different physiologic signal or sensor configuration in response to the change in patient functional state.

Figure 5:
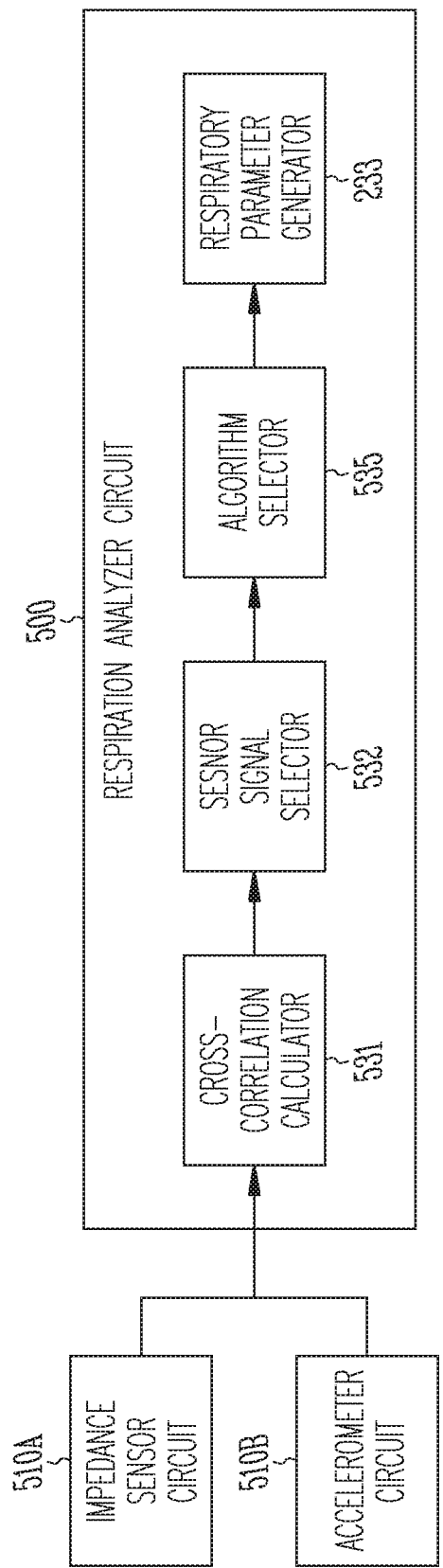
FIG. 5 illustrates generally yet another example of a respiration analyzer circuit.

FIG. 5 illustrates generally another example of respiration analyzer circuit 500, which may be an embodiment of the respiration analyzer circuit 231 of the cardiopulmonary event detector system 200. The respiration analyzer circuit 500 may include one or more of a cross-correlator 531, a sensor signal selector 532, an algorithm selector 535, and a respiratory parameter generator 233. The sensor signal selector 532 and the algorithm selector 535 are embodiments of the sensing configuration selector 232.

The cross-correlator 531 may be coupled to an impedance sensor circuit 510A and an accelerometer circuit 510B. The sensor circuits 510A-B are embodiments of two of the plurality of sensor circuit set 210 as illustrated in FIG. 2. The cross-correlator 531 is configured to calculate a correlation between an impedance signal such as sensed using the impedance sensor circuit 510A and a motion signal such as sensed using the accelerometer circuit 510B. The cross-correlation indicates the degree of congruence between the respiration-mediated change in impedance and the respiration-mediated motion.

The sensor signal selector 532 may select between the impedance signal and a motion signal based on the calculated cross-correlation. In an example, the cross-correlator 531 may continuously or periodically compute the cross-correlation between the impedance signal and the motion signal, and the sensor signal selector 532 may dynamically switch to a particular physiologic signal based on the calculated cross-correlation. A higher cross-correlation, such as one that exceeds a specific threshold, indicates that the impedance signal and the motion signal may have similar power or performance if they are each used for detecting respiration parameters. The sensor signal selector 532 may select the impedance signal because of the lower computational cost and less system resource requirement than the motion signal. If the cross-correlation falls below the specific threshold, indicting different power or performance between the two physiologic signals if they are each used for detecting respiration parameters, then the sensor signal selector 532 may switch to the computationally more costly, but more robust, motion signal to detect respiration parameters. The algorithm selector 535 may select a detection algorithm, and the respiratory parameter generator 233 may generate one or more respiration parameters from the selected physiologic signal using the selected detection algorithm.

Figure 6:
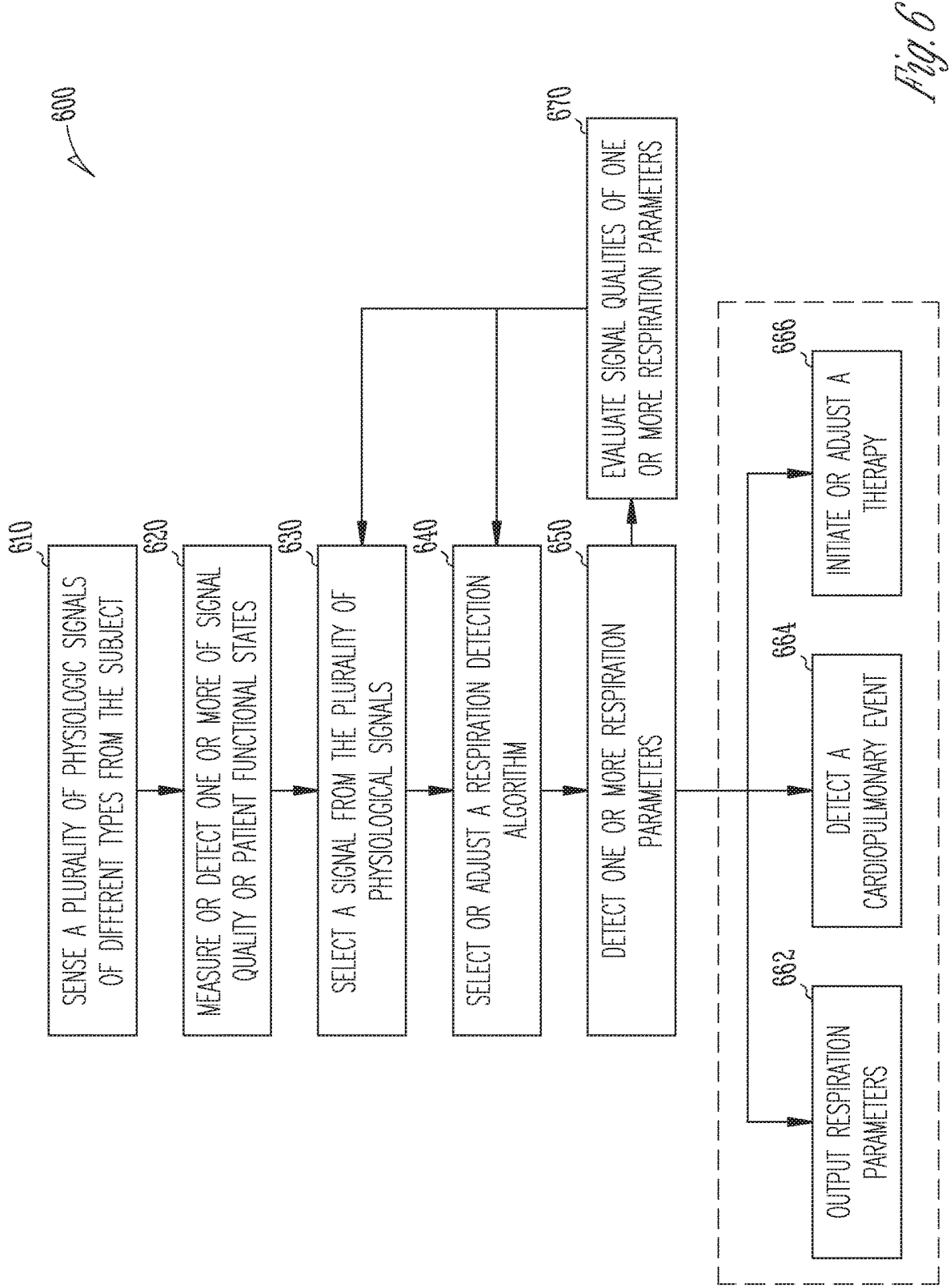
FIG. 6 illustrates an example of a method for detecting respiration from a subject.

FIG. 6 illustrates generally an example of a method 600 for detecting respiration from a subject. One or more respiration parameters, such as a respiratory cycle, an inspiration phase or an expiration phase, a respiratory rate, a tidal volume, or a minute ventilation, may be detected, and used in a process of detecting a cardiopulmonary event. The method 600 may be implemented and executed in one or more ambulatory medical devices (AMDs), such as implantable or wearable medical devices, or in a remote patient management system. In various examples, the method 600 may be implemented in and executed by the AMD 110, one or more devices in the external system 125, or the cardiopulmonary event detector system 200 or a modification thereof.

The method 600 commences at step 610, where a plurality of physiologic signals of distinct types may be sensed from a subject. The plurality of physiologic signals may be respectively sensed using sensor circuits each coupled to a respective physiologic sensor or sensing electrodes associated with the subject, such as the respiratory sensor circuits 210A, 210B, etc. as illustrated in FIG. 2. The sensed physiologic signals may each be indicative of respiration, such as a physiologic signal modulated by respiration. Examples of the sensed physiologic signals may include a surface or subcutaneous ECG signal, an intracardiac EGM, a heart rate signal, a thoracic or cardiac impedance signal, a chest wall motion signal, an abdomen motion signal, a blood pressure signal, an intracardiac pressure signal, coronary blood temperature signal, blood oxygen saturation signal, or heart sound signal, among others.

At 620, one or more of signal qualities of the plurality of physiologic signals, or patient functional states, may be detected. The signal quality may be expressed in terms of a signal-to-noise ratio (SNR), or signal intensity measure such as signal amplitude. Patient functional states may include physical activity, posture, or sleep/awake state. The physical activity may be detected using the physical activity sensor 411 coupled to an accelerometer. In an example, physical activity level may be represented by an average of a full-wave rectified acceleration signal over a specified time period. The posture may be detected using the posture sensor 411, and represented by a tilt angle sensed by a tilt switch. The sleep/awake state may be detected using the sleep/awake sensor 413, as discussed with reference to FIG. 4. In various examples, physical activity, posture, or sleep/awake state may be derived from one physiologic signal such as by passing an acceleration signal through different signal processing (e.g., signal filters with distinct pass bands and gains). In some examples, information of time of a day, such as a daytime or a nighttime of a day, may be acquired at 620, such as using the clock 414. The time of day may indirectly provide information about physically inactive, posture, or asleep/awake state according to daily schedule of a subject.

At 630, a physiologic signal may be selected from the plurality of physiologic signals for detecting respiration, such as using the sensing configuration selector 232 as illustrated in FIG. 2. In an example, the selection may be based on a signal characteristic, such as a signal quality measured by the signal quality analyzer 350. A physiologic signal with stronger signal intensity or higher SNR may be initially selected. In another example, a physiologic signal may be selected based on a computational cost associated with signal acquisition and processing, power consumption, data rate requirement, data storage requirement, among other measures of system or device resources. A physiologic signal associated with lower data acquisition and processing cost, lower power consumption, or less complex hardware support or system resource requirement (e.g., lower data sampling rate, data storage requirement, or bandwidth requirement for data communication between devices) may be initially selected. For example, the impedance signal may be initially chosen over the motion signal sensed by an accelerometer, because at least in some cases the impedance sensing and processing requires less power to operate. In yet another example, a sensor signal may be initially selected according to a balance between detection performance and the computational cost. The balance may be assessed using a composite cost-effectiveness metric, such as a linear or nonlinear combination of the gain achieved with a sensor signal such as accuracy rate of detecting respiration parameters under various conditions, and the cost associated with data acquisition and processing of a sensor signal, as well as cost associated with frequent switching between sensor signals. In some examples, the physiologic signal may be selected further using information about sensor configurations such as implant site and operation mode of a physiologic sensor, or environmental conditions.

In various examples, a physiologic signal may be selected using one or more patient functional states, such as physical activity, posture, or sleep/awake state. The selection may be executed using the respiration analyzer circuit 400. In an example, the selection is made between an impedance signal and a motion signal. Impedance, such as thoracic impedance, measures the electrical property of the chest and varies at inspiration and expiration phases, such that the impedance increases during inspiration and decreases during expiration. An example of the motion signal includes a chest wall motion signal representing chest expansion and contraction induced by respiration. The impedance and the motion signals may be detected by the impedance sensor circuit 510A and the accelerometer circuit 510B, respectively. Compared to impedance signal, motion signal may be more susceptible to interferences when the patient is physically active. In an example, impedance signal may be selected if the physical activity intensity or duration exceeds a respective threshold, or when a particular pattern of physical activity such as one indicating repetitive body motion is detected. When the physical activity intensity or duration falls below respective threshold indicative of a low activity level, motion signal may be selected to replace the impedance signal for respiration detection. In another example, the motion signal may be selected if a supine or a sitting posture is detected. When the posture sensor detects a change of posture such as from a supine or sitting position to a standing position, the impedance signal is selected to replace the motion signal for respiration detection. In another example, the motion signal may be selected if a sleep state is detected, and the impedance is selected when the patient is detected to be awake. In yet another example, the motion signal may be selected during nighttime or a specified time period when the patient is likely physically inactive, in a sitting or supine position, or during asleep. An impedance signal, such as a thoracic impedance signal, may be selected during daytime or a specified time period during a day when the patient is likely physically active, in a sitting or supine position, or during asleep.

Physiologic signal selection at 630 may additionally include a selection of a sensor configuration for sensing a physiologic signal, such as sensor location, implant site for an implantable physiologic monitor, or sensor operation mode. In an example, impedance may be sensed using various impedance vectors. In another example, motion may be sensed using a multi-axis accelerometer that can provide motion information along directions of two or more accelerometer axes. At 630, an impedance vector, or an accelerometer axis, that is less prone to patient posture or physical activity may be selected to detect respiration and to generate one or more respiration parameters.

At 640, a respiration detection algorithm may be selected or adjusted, such as using the algorithm selector 335. The respiration detection algorithm may be selected according to signal qualities, patient conditions, sensor configurations, environmental conditions, or a computational cost associated with the generation of the respiration parameters. For example, respirator rate may be detected using a peak detector method, a zero-crossing method, a correlation-based method, or a frequency-domain method. The peak detector and zero-crossing methods are computationally less demanding, and thus may be initially selected over the computationally more intensive methods such as correlation-based or frequency-domain methods.

At 650, one or more respiration parameters may be generated from the selected physiologic signal using the selected or adjusted respiration detection algorithm. Examples of the respiration parameters may include respiratory cycles, respiratory cycle period or respiratory rate, a tidal volume, a minute ventilation, a respiratory sound characteristic (such as a characteristic frequency of respiratory sound), or respiratory phase such as inspiration phase and expiration phase. The respiration parameters may include a respiratory pattern, such as RSBI, Cheyne-Stokes pattern, cluster breathing, Kussmaul's breathing, apneustic breathing, or ataxic breathing, among other patterns.

The respiration parameters may be output to a user or a process for further processing or to detect a medical condition. At 662, the one or more respiration parameters may be presented to a system user (e.g., a clinician), such as being displayed on a display screen of the user interface 220. The information may be presented in a table, a chart, a diagram, or any other types of textual, tabular, or graphical presentation formats. Hard copies of physiologic signals and the respiration parameters may be printed. In an example, alerts, alarms, emergency calls, or other forms of warnings may be generated to inform the system user about the detected respiration. The respiration parameters may be output to a process such as an instance of a computer program executable in a microprocessor.

Additionally or alternatively, at 664, the one or more respiration parameters may be used to detect a cardiopulmonary event, optionally together with other physiologic measurements, such as using the cardiopulmonary event detector circuit 234. Examples of the cardiopulmonary event may include CHF, pulmonary edema, sleep apnea, COPD, asthma, pulmonary embolism, or breathing disturbance or disorders associated with other medical conditions such as diabetic ketoacidosis. A respiration parameter may be trended over time, and a cardiopulmonary event may be detected if one or more of the respiration parameter trends satisfy respective conditions, such as exceeding a threshold or falling within a specific value range. In some examples, a composite respiratory index may be generated such as using a weighted combination of two or more of the respiration parameter trends. A cardiopulmonary event is detected if the composite respiratory index satisfies a specific condition.

Additionally or alternatively, at 666, the detected cardiopulmonary event may trigger a therapy delivered to the patient, such as using the therapy circuit 240. Examples of the therapy may include electrostimulation therapy delivered to the heart, a nerve tissue, other target tissue, a cardioversion therapy, a defibrillation therapy, or drug therapy. In some examples, the one or more respiration parameters may be used to modify an existing therapy, such as by adjusting a stimulation parameter or drug dosage. For example, in response to an increase in respiratory rate or minute ventilation which indicates elevated metabolic demand, an existing cardiac pacing therapy may be modified, such as by increasing pacing rate to meet the metabolic demand.

The method 600 may dynamically switch the physiologic signal or dynamically adjust the respiration detection algorithm based on the one or more respiration parameters detected at 650. At 670, signal qualities of the one or more respiration parameters may be evaluated, such as using the signal quality analyzer 350 as illustrated in FIG. 3. An indication of signal quality of the one or more respiration parameters may be generated. Depending on the signal quality indication, the method 600 may dynamically switch to a different physiologic signal than the originally selected physiologic signal. For example, if a respiration parameter derived from an impedance signal has an SNR falling below a threshold, or if the signal strength of a respiration parameter falls below a threshold indicating a reduced tidal volume, then a different physiologic signal, such as a motion signal from an accelerometer may be selected at 630. The dynamic switching of physiologic signal may also be triggered by other signal characteristics such as computational cost associated with signal acquisition and processing, and/or a change of patient function state such as a change in physical activity level, duration, or pattern, a different posture, or a different sleep/awake state.

The signal qualities of respiration parameters may also be used to dynamically switch to a different detection algorithm. For example, if the respirator rate estimated using the zero-crossing method has a poor quality such as large variability of the respiratory rate estimates, or substantial amount of failure in detecting the zero-crossings, then the zero-crossing method may be adjusted such as by adjusting signal filter settings or a detection threshold. Alternatively, the method may switch to a different detection algorithm, such as correlation-based method, a frequency-domain method, or other computationally more intensive or costly algorithm at 640.

Figure 7:
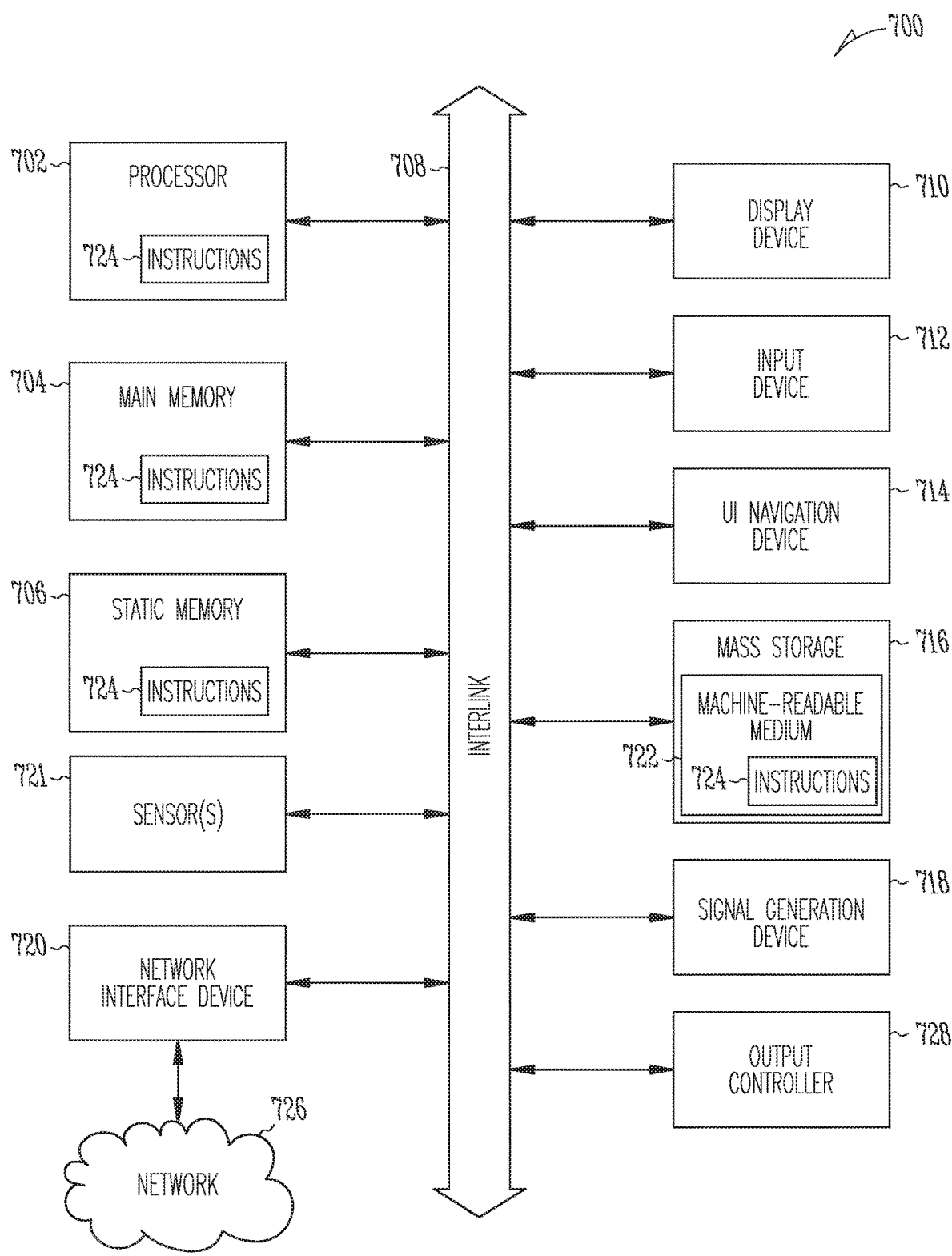
FIG. 7 illustrates generally a block diagram of an example machine upon which any one or more of the techniques discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
a respiration analyzer circuit configured to:
receive an impedance signal and a motion signal sensed from a subject;
determine a correlation between the impedance signal and the motion signal;
select a signal from the impedance signal and the motion signal based on the determined correlation; and
compute a respiration parameter using the selected signal.

2. The system of claim 1, wherein the respiration analyzer circuit is configured to receive the impedance signal from a first sensor circuit and the motion signal from a second sensor circuit different from the first sensor circuit, and to switch from the selected signal to an unselected signal of the impedance signal or the motion signal based on a change in the determined correlation.

3. The system of claim 2, wherein the first sensor circuit is an impedance sensor circuit configured to sense the impedance signal, and the second sensor circuit is an accelerometer or a gyroscope sensor circuit configured to sense the motion signal.

4. The system of claim 1, wherein the respiration analyzer circuit is configured to detect a physical activity level or a posture of the subject, and to select the signal from the impedance signal and the motion signal using the detected physical activity level or posture.

5. The system of claim 1, wherein the respiration analyzer circuit is configured to detect a sleep or awake state of the subject, and to select the signal from the impedance signal and the motion signal using the detected sleep or awake state.

6. The system of claim 1, wherein the respiration analyzer circuit is configured to select the signal using information of time of a day when the impedance signal and the motion signal are sensed.

7. The system of claim 1, wherein the respiration analyzer circuit is configured to determine computational complexity for sensing the impedance signal and the motion signal, and to switch from the impedance signal to the motion signal to compute a respiration parameter if a respiration parameter computed using the impedance signal satisfies a specific condition, the motion signal associated with more computational complexity of signal acquisition and processing than the impedance signal.

8. The system of claim 1, wherein:
to select the signal includes to switch from the impedance signal to the motion signal if the determined correlation falls below a threshold.

9. The system of claim 1, wherein the respiration analyzer circuit is further configured to determine, based on a physical activity level or a posture of the subject, one or more of:
an impedance vector for sensing the impedance signal; or
an accelerometer axis for sensing the motion signal.

10. The system of claim 1, comprising a cardiopulmonary event detector configured to detect a cardiopulmonary event using the computed respiration parameter.

11. The system of claim 10, comprising a therapy circuit configured to deliver a therapy in response to the detection of the cardiopulmonary event.

12. The system of claim 1, wherein the respiration parameter includes one or more of a respiratory rate (RR), a tidal volume (TV), a minute ventilation (MV), or a rapid shallow breathing index (RSBI), or a trend of one or more of the RR, TV, MV, or RSBI.

13. The system of claim 1, wherein the impedance signal is detected using a first detection algorithm, and the motion signal is detected using a second detection algorithm.

14. The system of claim 13, comprising a respiration sensor configured to sense the impedance signal using the first detection algorithm, and to sense the motion signal using the second detection algorithm, wherein the first detection algorithm has a different computational complexity than the second detection algorithm.

15. A method for sensing respiration from a subject via a medical system, the method comprising:
sensing from the subject an impedance signal and a motion signal using at least one sensor circuit;
determining a correlation between the impedance signal and the motion signal;
selecting a signal from the impedance signal and the motion signal using a respiration analyzer circuit based on the determined correlation; and
computing, via the respiration analyzer circuit, a respiration parameter using the selected signal.

16. The method of claim 15, comprising detecting a functional state of the subject including one or more of physical activity, posture, or sleep or awake state of the subject, wherein selecting the signal from the impedance signal and the motion signal is based on the detected functional state.

17. The method of claim 15, comprising:
determining computational complexity for sensing the impedance signal and the motion signal:
switching from the impedance signal to the motion signal if a respiration parameter computed using the impedance signal satisfies a specific condition, wherein the motion signal differs from the impedance signal and is associated with more computational complexity of signal acquisition and processing than the impedance signal; and
computing the respiration parameter using the motion signal.

18. The method of claim 15,
wherein selecting the signal includes switching from the impedance signal to the motion signal if the determined correlation falls below a threshold.

19. The method of claim 15, wherein the impedance signal is detected using a first detection algorithm, and the motion signal is detected using a second detection algorithm.

20. The method of claim 15, comprising detecting a cardiopulmonary event using the computed respiration parameter.

* * * * *